United States Patent [19]

Nishihara et al.

[11] Patent Number: 5,420,350

[45] Date of Patent: May 30, 1995

[54] BIS-BIGUANIDE COMPOUND USEFUL AS A DISINFECTANT

[76] Inventors: Akira Nishihara; Akihiro Nakamura; Tsunetoshi Honda, all of Mitsubishi Materiaru Kabushiki Kaisha Chuo-kenkyusho-nai 1-297, Kitabukuro-cho, Omiya-shi, Saitama-ken; Michio Harada, 4-3-16, Igusa, Suginami-ku, Tokyo; Maki Takizawa, 13-11-808, Minami-cho, Hanno-shi, Saitama-ken, all of Japan

[21] Appl. No.: 298,300

[22] Filed: Sep. 1, 1994

[30] Foreign Application Priority Data

Sep. 9, 1993 [JP] Japan ................... 5-224582

[51] Int. Cl.⁶ ............... C07C 279/06; C07C 279/18; A01N 37/52
[52] U.S. Cl. .................... 564/235; 424/405; 562/587; 564/236
[58] Field of Search ............... 564/235, 236; 514/635, 514/554; 424/405; 562/587

[56] References Cited

U.S. PATENT DOCUMENTS

| | | | |
|---|---|---|---|
| 2,684,924 | 7/1954 | Rose et al. | 167/30 |
| 2,990,425 | 6/1961 | Senior | 260/501 |
| 3,468,898 | 9/1969 | Cutler et al. | 260/301 |
| 3,860,648 | 12/1975 | Diamond et al. | 260/565 |
| 4,022,834 | 5/1977 | Gunderson | 260/564 B |
| 4,053,636 | 10/1977 | Eustis, III et al. | 424/326 |
| 4,067,962 | 1/1978 | Juneja | 424/52 |
| 4,198,392 | 4/1980 | Juneja | 424/48 |
| 4,420,484 | 12/1983 | Gorman et al. | 424/326 |
| 4,900,721 | 2/1990 | Bansemir et al. | 514/25 |
| 4,942,041 | 7/1990 | Guhl et al. | 424/613 |

FOREIGN PATENT DOCUMENTS 2262283  6/1993  United Kingdom .

*Primary Examiner*—José G. Dees
*Assistant Examiner*—Barbara S. Frazier

[57] ABSTRACT

A novel bis-biguanide compound suitable for use as a disinfectant has the following formula:

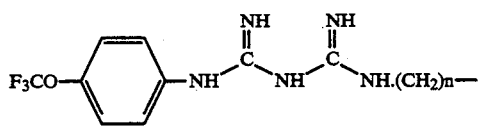

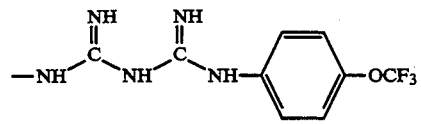

where n is an integer from 2 to 10 inclusive. A pharmaceutically acceptable salt, particularly gluconate salt of the compound is also useful as a disinfectant. The bis-biguanide compound has germicidal activities comparable to those of widely used chlorhexidine with respect to width of antibacterial spectrum and is superior to chlorhexidine in immediate effectiveness. It exhibits excellent germicidal activities against Pyocyaneus bacilli, on which chlorhexidine has poor effect.

10 Claims, No Drawings

BIS-BIGUANIDE COMPOUND USEFUL AS A DISINFECTANT

BACKGROUND OF THE INVENTION

The present invention relates to a novel bis-biguanide compound having germicidal activity and a disinfectant composition containing the same.

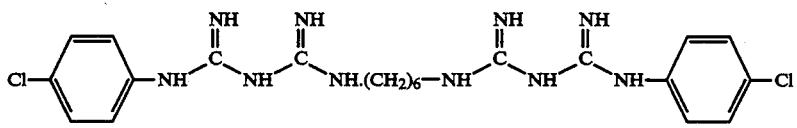

is a bis-biguanide compound developed in 1954 as a disinfectant. This compound exhibits disinfecting or germicidal activities on a wide range of general bacteria and is widely used because of its quick effect and low toxicity. Especially, it is used as a gluconate salt, which has high solubility in water, for disinfection of hands and fingers in hospitals, body skin to be operated on, and medical instruments, particularly surgical instruments.

However, chlorhexidine has a defect that it is less effective against some Gram-negative bacteria, especially Pyocyaneus bacilli, typical of which is *Pseudomonas aeruginosa*. Furthermore, recently Pyocyaneus bacillus strains and *Pseudomonas cepacia* strains, which are resistant to this disinfectant, have been reported to be a problem in medical institutions. Chlorhexidine sometimes causes shock symptoms when it is administered to mucous membranes in a conventional concentration. Therefore, administration thereof to mucous membranes other than conjunctivae is now prohibited.

Under these circumstances, a substitute for chlorhexidine which retains the wide antibacterial spectrum of chlorhexidine and possesses germicidal effect and medial applicability superior to that of chlorhexidine has been sought. Thus, there is a demand for a novel chlorhexidine-type disinfectant for medical use which can be used in a concentration low enough to be safely applicable to mucous membranes, has improved germicidal activity especially against Pyocyaneus bacillus strains, against which chlorhexidine is no longer effective, and is suitable for use as a topical disinfectant for surgical operations.

SUMMARY OF THE INVENTION

It has been found that a compound having the same chemical formula as chlorhexidine except that the chlorine substituent on each benzene ring is replaced by a trifluoromethoxy group has improved germicidal activities, and that its activities are particularly high against Pyocyaneus bacilli.

The present invention provides a novel bis-biguanide compound of the following formula:

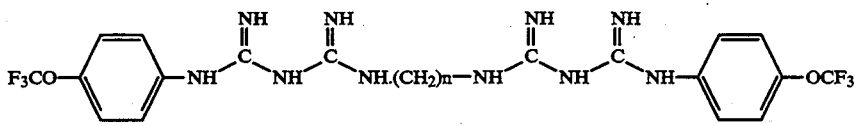

where n is an integer from 2 to 10 inclusive, and a salt thereof. Preferably, n is an integer from 3 to 8 inclusive and most preferably it is 6.

In another aspect, the present invention provides a disinfectant composition comprising a bis-biguanide compound of the above formula (I) or a pharmaceutically acceptable salt thereof as an active ingredient.

The pharmaceutically acceptable salt includes salts with a mineral acid such as hydrochloric acid, hydrofluoric acid, or sulfuric acid, as well as salts with an organic acid, particularly a carboxylic acid such as gluconic acid, acetic acid, lactic acid, tartaric acid, or oxalic acid. Particularly preferred is a gluconate salt, i.e., a salt with gluconic acid, due to its high solubility in water.

The bis-biguanide compound according to the present invention can be synthesized generally following a reaction scheme known for the synthesis of chlorhexidine, which is described, e.g., in J. Chem. Soc., 4422 (1956), by replacing some of the starting materials used.

The synthesis can be achieved, for example, by reacting a diamine of the formula $H_2N(CH_2)_nNH_2$ (where n is an integer from 2 to 10 inclusive) with sodium dicyanamide to form a 1,n-bis($N^3$-cyano-$N^1$-guanidino)alkane of formula (II) below. The reaction product (II) is then reacted with a stoichiometric amount or a slight excess of 4-trifluoromethoxyaniline hydrochloride of formula (III) below in a polar solvent such as 2-ethoxyethanol or butanol to give the desired bis-biguanide compound (I) in the form of hydrochloride. Preferably, the latter reaction is usually conducted by heating the reaction mixture to reflux.

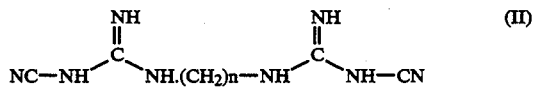

The resulting hydrochloric acid may be neutralized with an alkali such as sodium hydroxide to give the free bis-biguanide compound (I), which may further be converted into a salt with another acid such as gluconic acid by addition of the acid.

The bis-biguanide compound according to the present invention and its salt exhibit improved germicidal activities against a wide variety of bacteria including Pyocyaneus bacilli as evidenced in the following examples. Therefore, they are suitable for use as a disinfectant to give a disinfectant composition comprising a bis-biguanide compound (I) or a pharmaceutically acceptable salt thereof as an active ingredient.

The form of the disinfectant composition is not critical. Generally, it is a solution of the active ingredient in water, in an alcohol, or in a mixture of water and an alcohol. In such cases, the active ingredient is preferably in the form of a salt of compound (I), and most preferably a gluconate salt is used in view of its high solubility in water. The concentration of the solution is preferably in the range of 0.01%–1.0% and more preferably 0.01%–0.2% by weight. The solution may further contain a surfactant or other one or more auxiliary agents and/or an additional disinfectant.

The concentration of a disinfectant solution in practical use is normally selected in view of the germicidal activity of the disinfectant used as an active ingredient against the bacterial species for which the disinfectant is least effective. Conventional disinfectant solutions containing chlorhexidine have a concentration of 0.1%–4% by weight and such a concentration, particularly at a level exceeding 0.2%, is so high that the solution may cause shock symptoms when administered to mucous membranes.

In contrast, the bis-biguanide compound (I) or its salt can be used effectively as a solution having a concentration as low as 0.01%–0.2% by weight. Such a solution can be administered to mucous membranes and injured areas without causing shock symptoms. Therefore, the solution can be applied to wider areas of human bodies compared to a conventional chlorhexidine solution.

The disinfectant composition may be in the form of tablets, which can be used by dissolving them in water and/or an alcohol. Furthermore, the bis-biguanide compound (I) or its salt may be incorporated into a substrate material to provide the material with antibacterial activities.

The following examples are presented to further illustrate the present invention. These examples are to be considered in all respects as illustrative and not restrictive.

EXAMPLE 1

Synthesis of Compound (I) (n=6)

In 2-ethoxyethanol as a solvent, 12.5 g (50 mmol) of 1,6-bis($N^3$-cyano-$N^1$-guanidino)hexane and 23.5 g (110 mmol) of 4-trifluoromethoxyaniline hydrochloride were reacted by heating to reflux for 20 hours. The precipitates which separated out after cooling were collected by filtration and were combined with additional precipitates recovered from the filtrate by concentration and washed with ethanol. The combined precipitates were recrystallized from an aqueous 50 wt % acetic acid solution to give 19.5 g of a white solid, which was the hydrochloride of a compound of formula (I) in which n is 6.

The white solid was then dissolved in 150 ml of 6N HCl and 150 ml of an aqueous 8N NaOH solution were added dropwise to the resulting solution under cooling in an ice bath, The precipitates formed by the reaction were collected, washed with water, and recrystallized from an ethanol-water mixed solvent (7/3 in volume ratio) to give the desired compound (I) (n=6) as a free base. The NMR, IR, and mass spectrum data of this compound are as follows.

NMR spectrum: $^1$H-NMR (270 MHz, DMSO-$d_6$/TMS); $\delta$1.32 ppm (brs, 4H), $\delta$1.47 ppm (m, 4H), $\delta$3.12 ppm (t, 4H, J=6.8 Hz), $\delta$3.37 ppm (brs, 4H), $\delta$7.19 ppm (brs, 8H), $\delta$6.6–8.0 ppm (brs, 6H); $^{13}$C-NMR (67.8 MHz, DMSO-$d_6$/TMS); $\delta$26.04 ppm, $\delta$28.86 ppm, $\delta$40.54 ppm, $\delta$120.18 ppm (q, $J_{CF}$=255.3 Hz), $\delta$121.51 ppm, $\delta$122.85 ppm, $\delta$142.52 ppm, $\delta$145.02 ppm, $\delta$156.48 ppm, $\delta$159.02 ppm; $^{19}$F-NMR (254 MHz, DMSO-$d_6$/TMS); $\delta$-56.66 ppm(s); IR Absorption Spectrum (KBr tablet, cm$^{-1}$): 724, 1160, 1252, 1382, 1425, 1508, 1550, 1612, 2940, 3190, 3330; Mass Spectrum (70 eV, m/e): 69 (54.7%), 105 (30.2%), 108 (20.2%), 133 (90.7%), 202 (100%), 330 (1.4%), 443 (3.2%), 604 (0.2%).

EXAMPLE 2

Synthesis of Compound (I) (n=3)

Following the procedure described in Example 1 except that 10.4 g (50 mmol) of 1,3-bis($N^3$-cyano-$N^3$-guanidino)propane was used in place of 1,6-bis($N^3$-cyano-$N^1$-guanidino)hexane and that the reaction was performed by heating to reflux for 15 hours, 19.5 g of the hydrochloride of a compound of formula (I) where n is 3 were obtained as a white solid. The hydrochloride was then neutralized and recrystallized in the same manner as described in Example 1 to give the desired compound (I) (n=3) as a free base, which had the following NMR, IR, and mass spectrum.

NMR spectrum: $^1$H-NMR (270 MHz, DMSO-$d_6$/TMS); $\delta$1.68 ppm (brs, 2H), $\delta$3.39 ppm (brs, 4H), $\delta$7.24 ppm (brs, 8H), $\delta$6.4–8.0 ppm (brs, 6H); $^{13}$C-NMR (67.8 MHz, DMSO-$d_6$/TMS); $\delta$27.55 ppm, $\delta$41.37 ppm, $\delta$121.34 ppm (q, $J_{CF}$=253.5 Hz), $\delta$122.43 ppm, $\delta$123.78 ppm, $\delta$145.87 ppm, $\delta$147.15 ppm, $\delta$158.48 ppm, $\delta$162.11 ppm; $^{19}$F-NMR (254 MHz, DMSO-$d_6$/TMS); $\delta$-57.26 ppm(s); IR Absorption Spectrum (KBr tablet, cm$^{-1}$): 784, 1170, 1356, 1428, 1520, 1550, 1625, 2940, 3200, 3310; Mass Spectrum (70 eV, m/e): 69 (78.7%), 105 (30.2%), 108 (20.2%), 133 (40.3%), 202 (100%), 401 (2.0%), 562 (0.5%).

EXAMPLE 3

Synthesis of Compound (I) (n=10)

The procedure described in Example 1 was repeated except that 15.3 g (50 mmol) of 1,10-bis($N^3$-cyano-$N^1$-guanidino)decane were used in place of 1,6-bis($N^3$-cyano-$N^1$-guanidino)hexane. The hydrochloride of compound (I) where n is 10 was obtained as a white solid in an amount of 16.5 g. The final free base product, which was obtained by dissolving the hydrochloride in 200 ml of 6N HCl followed by dropwise addition of 200 ml of a 6N NaOH solution and which was a compound of formula (I) where n is 10, had the following NMR, IR, and mass spectrum.

NMR spectrum: $^1$H-NMR (270 MHz, DMSO-$d_6$/TMS); $\delta$1.34 ppm (brs, 16H), $\delta$3.12 ppm (brs, 4H), $\delta$3.70 ppm (brs, 4H), $\delta$7.33 ppm (brs, 8H), $\delta$6.6–8.0 ppm (brs, 6H); $^{13}$C-NMR (67.8 MHz, DMSO-$d_6$/TMS); $\delta$26.35 ppm, $\delta$28.75 ppm, $\delta$28.33 ppm, $\delta$33.37 ppm, $\delta$42.54 ppm, $\delta$119.22 ppm (q, $J_{CF}$=254 Hz), $\delta$122.85 ppm, $\delta$123.73 ppm, $\delta$143.25 ppm, $\delta$147.20 ppm, $\delta$158.84 ppm, $\delta$160.32 ppm; $^{19}$F-NMR (254 MHz, DMSO-$d_6$/TMS); $\delta$-56.23 ppm(s); IR Absorption Spectrum (KBr tablet, cm$^{-1}$): 678, 1174, 1260, 1375, 1510, 1570, 1620, 3150, 3380; Mass Spectrum (70 eV, m/e): 69 (84.1%), 105 (20.3%), 108 (15.7%), 133 (84..0%), 202 (100%), 499 (0.5%).

EXAMPLE 4

Preparation of Gluconate Salt in Solution

To each compound of Formula (I) obtained in Examples 1 to 3, a 50 wt % gluconic acid solution prepared by dissolving gluconic acid in a molar amount twice the molar amount of the compound (I) in distilled water was added. The resulting solution, which contained digluconate salt of the compound (I), could be diluted with distilled water to a predetermined concentration suitable for disinfection.

EXAMPLE 5

Evaluation of Germicidal Activity of Compound (I) (n=6)

Germicidal activity of the compound of formula (I) (n=6) prepared in Example 1 as a disinfectant was evaluated by the minimum growth inhibition concentration (MIC) method based on the standard method specified by the Japan Society of Chemotherapy and by the phenol coefficient method.

(A) MIC method:

A portion of the aqueous solution of the digluconate salt of compound (I) (n=6) prepared in Example 4 was evaporated to dryness on a water bath, and the remaining dried salt was dissolved in acetic anhydride (potentiometric titration grade). The concentration of the resulting gluconate salt solution was determined by potentiometric titration using an aqueous perchloric acid solution. The gluconate solution was then diluted by different factors with sterilized water to give solutions having various predetermined concentrations.

One (1) ml aliquots of each solution were separately placed in Petri dishes, and 9 ml of Mueller-Hinton agar (Difco) were added to each dish and thoroughly mixed with the solution therein. The resulting mixtures were used as culture media for measuring sensitivity. The concentrations of the gluconate salt in the media were 200 μg/ml and $2^N$ times where N is from −8 to 2.

Separately, the microorganism strains indicated in Table 1 were subcultured in propagation media prepared by using Mueller-Hinton broth (Difco) for 24 hours at 37° C. The microorganism concentration in each medium was then adjusted to $10^6$ cells/ml to give a culture for inoculation.

A series of culture media for measuring sensitivity prepared above having different concentrations was inoculated with the culture using an inoculation rod and incubated for 24 hours at 37° C. After the incubation, each medium was observed for growth of the microorganism, and the minimum inhibition concentration (MIC) at which growth of the microorganism was completely inhibited was determined. The results are shown in Table 1 along with the results of a comparative test using chlorhexidine as a disinfectant.

TABLE 1

| Microorganism | MIC (μg/ml) CHXD | (I) |
|---|---|---|
| *Alcaligenes faecalis* IPO 13111 | 50 | 6.25 |
| *Achromobacter xylosoxidans* RIMD 0101001 | 50 | 50 |
| *Flavobacterium meningosepticum* RIMD 0614002 | 200 | 200 |
| *Klebsiella pneumoniae* IID 865 | 3.13 | 3.13 |
| *Proteus vulgaris* IID 874 | 200 | 12.5 |
| *Pseudomonas aeruginosa* IID 1042 | 200 | 25 |
| *Pseudomonas aeruginosa* (clinically collected) | 50 | 25 |
| *Serratia marcescens* IID 602 | 6.25 | 6.25 |
| *Escherichia coli* IID 861 | 1.56 | 3.13 |
| *Escherichia coli* IID 951 | 1.56 | 3.13 |
| *Escherichia coli* NIHJ JC-2 | 1.56 | 3.13 |
| *Pseudomonas cepacia* (collected Chiba Univ.) | 100 | 50 |
| *Staphylococcus epidermidis* IID 866 | 1.56 | 1.56 |
| *Staphylococcus aureus* FDA 209-P | 1.56 | 1.56 |
| *Staphylococcus aureus* (clinically collected MRSA) | 3.13 | 3.13 |
| *Staphylococcus aureus* (clinically collected MRSA) | 3.13 | 3.13 |

CHXD = chlorhexidine digluconate; (I) = Compound (I) as digluconate salt

As can be seen from Table 1, a compound (I) (n=6) according to the present invention exhibited germicidal activities against *Pseudomonas aeruginosa*, *Proteus vulgaris*, and *Alcaligenes faecalis* at concentrations as low as ¼–⅛ the effective concentration for chlorhexidine. Against the other microorganisms, the compound was effective approximately at the same level as chlorhexidine.

(B) Phenol Coefficient Method (test for immediate effect):

Immediate effect of the compound was evaluated in accordance with the phenol coefficient method described in "Directions for Hygienic Tests" compiled by the Ministry of Health and Welfare of Japan. The method is as follows.

(1) Culture medium:

Each 10 ml of the bouillon described below were taken into test tubes and were sterilized with high pressure steam at 121° C. for 20 minutes.

| | |
|---|---|
| Peptone (Nippon Seiyaku) | 10 g |
| Meat extract (Kyokuto Seiyaku) | 5 g |
| NaCl (Kokusan Kagaku, special grade) | 5 g |
| purified water | 1000 ml |
| pH 6.8 | |

(2) Test method:

Diluted solutions of a series of concentrations of the test compound (I) as digluconate salt were prepared for each of the microorganisms listed in Table 2. Ten (10) ml aliquots of the diluted solutions were put into appraisal test tubes, and the test tubes were placed in a thermostat water bath kept at 20° C.

Separately, each microorganism was subcultured for three generations in the above-described bouillon medium for testing disinfectants (for from 18 to 24 hours at 37° C.). One (1) ml aliquots of each of the resulting cultures were added to the above-described appraisal test tubes containing a series of diluted solutions, respectively, and mixed thoroughly.

After 0.5 and 5 minutes, a 0.1 ml aliquot of the mixture in each appraisal test tube was taken to inoculate a predetermined amount of the bouillon medium for testing disinfectants. The inoculated media were then incubated for 48 hours at 37° C. and observed to determine whether growth of the microorganism was inhibited (marked as "−") or not inhibited (marked as "+"). The results are shown in Table 2 below.

TABLE 2

| | Concen- | Contact Time (min) | | | |
|---|---|---|---|---|---|
| | tration | Compound (I) | | Chlorhexidine | |
| Microorganism | (ppm) | 0.5 | 5.0 | 0.5 | 5.0 |
| *Escherichia coli* | 50 | − | − | − | − |
| IID 951 | 25 | + | − | + | − |
| | 10 | + | + | + | + |
| *Pseudomonas aerugi-* | 500 | − | − | − | − |
| *nosa* IID 1042 | 250 | − | − | + | − |
| | 100 | − | − | + | + |
| | 50 | + | + | + | + |
| *Staphylococcus aureus* | 10 | − | − | + | − |
| FDA 209-P | 7.5 | − | − | + | − |
| | 5 | − | − | + | − |

Compound (I) and Chlorhexidine, both digluconate salt

As can be seen from Table 2, the immediate activity of compound (I) (n=6) according to the present invention was superior to that of chlorhexidine, particularly against Pyocyaneus and Staphylococcus bacilli.

EXAMPLE 6

Compounds of formula (I) in which n was 2, 3, 5, 8, and 10, which were prepared in Examples 2 and 3 or in the same manner as described in Example 1, were evaluated for germicidal activities against *Ps. aeruginosa, Serratia marcescens, E. coli*, and *Staphylococcus aureus* by the MIC method as described in Example 5. The minimum growth inhibition concentrations (MIC) which were determined are shown in Table 3 below along with the results of Example 5 for the compound (I) in which n was 6.

TABLE 3

| Microorganism | MIC (μg/ml) | | | | | |
|---|---|---|---|---|---|---|
| | n = 2 | n = 3 | n = 5 | n = 6 | n = 8 | n = 10 |
| *Pseudomonas aeruginosa* IID 1042 | 200 | 100 | 25.0 | 25.0 | 25.0 | 50 |
| *Serratia marcescens* IID 602 | 100 | 12.5 | 12.5 | 6.25 | 6.25 | 12.5 |
| *Escherichia coli* IID 951 | 50 | 12.5 | 6.25 | 3.13 | 12.5 | 25.0 |
| *Staphylococcus aureus* FDA 209-P | 12.5 | 1.56 | 1.56 | 1.56 | 1.56 | 12.5 |

Test compound: digluconate of compound (I) having the indicated value for "n".

As can be seen from the results of Examples 5 and 6, the bis-biguanide compounds of formula (I) and their salts are effective as disinfectants, and their germicidal activities are comparable to those of widely used chlorhexidine with respect to width of antibacterial spectrum. They are superior to chlorhexidine in immediate effectiveness, and are also superior in that they exhibit excellent germicidal activity against Pyocyaneus bacilli, on which chlorhexidine has poor effect.

Accordingly, the bis-biguanide compounds and their salts are effective as disinfectants in the medical field, particularly for disinfection of body skin and surgical instruments. Compared to chlorhexidine they can be used in a lower concentration, causing less irritation to mucous membranes, and therefore it is expected to be applicable to mucous membranes to which chlorhexidine cannot be applied.

It will be appreciated by those skilled in the art that numerous variations and modifications may be made to the invention as described above with respect to specific embodiments without departing from the spirit or scope of the invention as broadly described.

What is claimed is:

1. A bis-biguanide compound of the following formula:

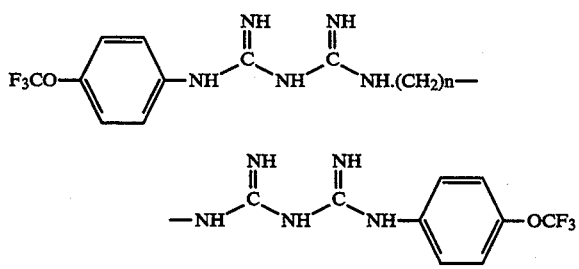

where n is an integer from 2 to 10 inclusive, and a salt thereof.

2. The bis-biguanide compound of claim 1, wherein n is an integer from 3 to 8 inclusive.

3. The bis-biguanide compound of claim 1, wherein the compound is in the form of a salt with an acid selected from the group consisting of mineral acids and carboxylic acids.

4. The bis-biguanide compound of claim 3, wherein the acid is gluconic acid.

5. A disinfectant composition comprising a bis-biguanide compound of the following formula:

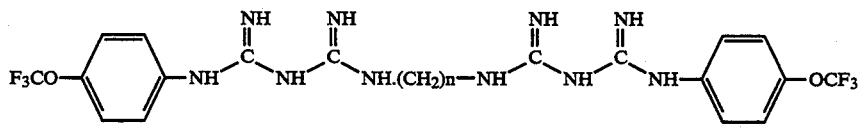

where n is an integer from 2 to 10 inclusive, or a pharmaceutically acceptable salt thereof as an active ingredient.

6. The disinfectant composition of claim 5, wherein n is an integer from 3 to 8 inclusive.

7. The disinfectant composition of claim 6, wherein the compound is in the form of a salt with an acid selected from the group consisting of mineral acids and carboxylic acids.

8. The disinfectant composition of claim 7, wherein the compound is in the form of a salt with gluconic acid.

9. The disinfectant composition of claim 8, wherein the gluconic acid salt is in the form of a solution in water, an alcohol, or a mixture of water and an alcohol as a solvent.

10. The disinfectant composition of claim 9, wherein the solution has a concentration of 0.01–1.0 wt %.

* * * * *

UNITED STATES PATENT AND TRADEMARK OFFICE
CERTIFICATE OF CORRECTION

PATENT NO. :      5,420,350
DATED      :      May 30, 1995
INVENTOR(S) :    NISHIHARA et al.

It is certified that error appears in the above-indentified patent and that said Letters Patent is hereby corrected as shown below:

ON THE TITLE PAGE:
Between items [76] and [21] insert:

--[73] Assignees: Mitsubishi Materials Corporation and Yoshida Pharmaceutical Co., Ltd., both of Tokyo, JAPAN--.

Signed and Sealed this

Sixteenth Day of January, 1996

Attest:

BRUCE LEHMAN

*Attesting Officer*    *Commissioner of Patents and Trademarks*